United States Patent [19]

Chi et al.

[11] Patent Number: 5,782,759
[45] Date of Patent: Jul. 21, 1998

[54] CARDIOVASCULAR TESTING DEVICE

[75] Inventors: Liguo Chi, Ann Arbor; Lori Saganek, Canton; Kim P. Gallagher, Ann Arbor; Andrew Uprichard, Grass Lake, all of Mich.

[73] Assignee: Warner-Lambert Company, Morris Plains, N.J.

[21] Appl. No.: 774,671

[22] Filed: Dec. 30, 1996

[51] Int. Cl.$^6$ .................................................. A61B 5/00
[52] U.S. Cl. .................................................. 600/369
[58] Field of Search .................................. 600/368, 369

[56] References Cited

PUBLICATIONS

Peters et al., "The Characterisation of Thrombus Development in an Improved Model of Arterio–Venous Shunt Thrombosis in the Rat . . . ", Thrombosis and Haemostasis, vol. 65, pp. 268–274, Mar. 1991.

Inhibition of Platelet–Dependent Thrombosis by Local Delivery of Heparin With a Hydrogel–Coated Balloon; G. L. Nunes, M.D., et al., Circulation, vol. 92, No. 7, Oct. 1, 1995, pp. 1697–1700.

Antithrombotic Effects of Orally Active Synthetic Antagonist of Activated Factor X in Nonhuman Primates; T. Yokoyama, PhD., et al.; Circulation, vol. 92, No. 3, Aug. 1, 1995, pp. 485–491.

An In Vitro Circulation Model for Thrombosis; Influence of Circulating Plasmas on the Binding of Monoclonal Antibodies to Human Fibrin Clots; F. J. McEvoy, et al., Fibrinoloysis, (1995) pp. 309–315.

Experimental Thrombosis on a Collagen Coated Arterioarterial Shunt in Rats: A Pharmacological Model to Study Antithrombotic Agents Inhibiting Thrombin Formation and Platelet Deposition; M. Freund, et al., Thrombosis and Haemostatis, 69 (5) pp. 515–521 (1993).

A Comparative Study of Prothrombinase and Thrombin Inhibitors in a Novel Rabbit Model of Non–Occlusive Deep Vein Thrombosis; S. Hollenbach, et al.; Thrombosis and Haemostatis; 71 (3) pp. 357–362; (1994).

Platelet Interactions with Dacron Vascular Grafts; S. R. Hanson, et al.; Arteriosclerosis 5:595–603; Nov./Dec. 1985.

*Primary Examiner*—Jennifer Bahr
*Assistant Examiner*—Eric F. Winakur
*Attorney, Agent, or Firm*—Charles W. Almer

[57] ABSTRACT

The present invention relates to a method and device for creating and testing arterial and venous thrombotic conditions. The invention includes a tube which is inserted into a blood vessel of an animal. The tube contains one or more strands upon which various materials, such as procoagulants and anticoagulants may be placed. Blood flows through the tube and clots form on the threads. After the completion of the test, the tube is removed from the animal, the strands are removed from the tube and the clots may be measured and weighed. In a preferred embodiment, a flowmeter may be connected to the blood vessel to measure the blood flow so that the clot measurements may be correlated with the blood flow.

17 Claims, 2 Drawing Sheets

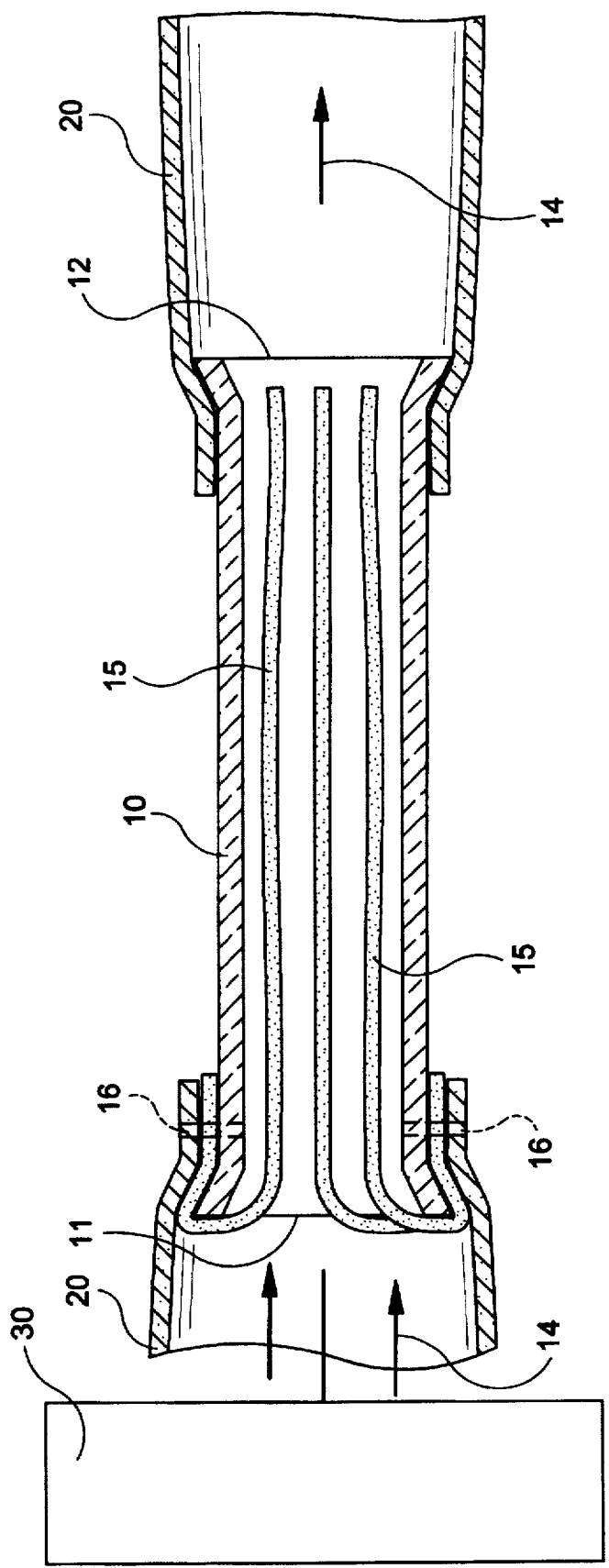

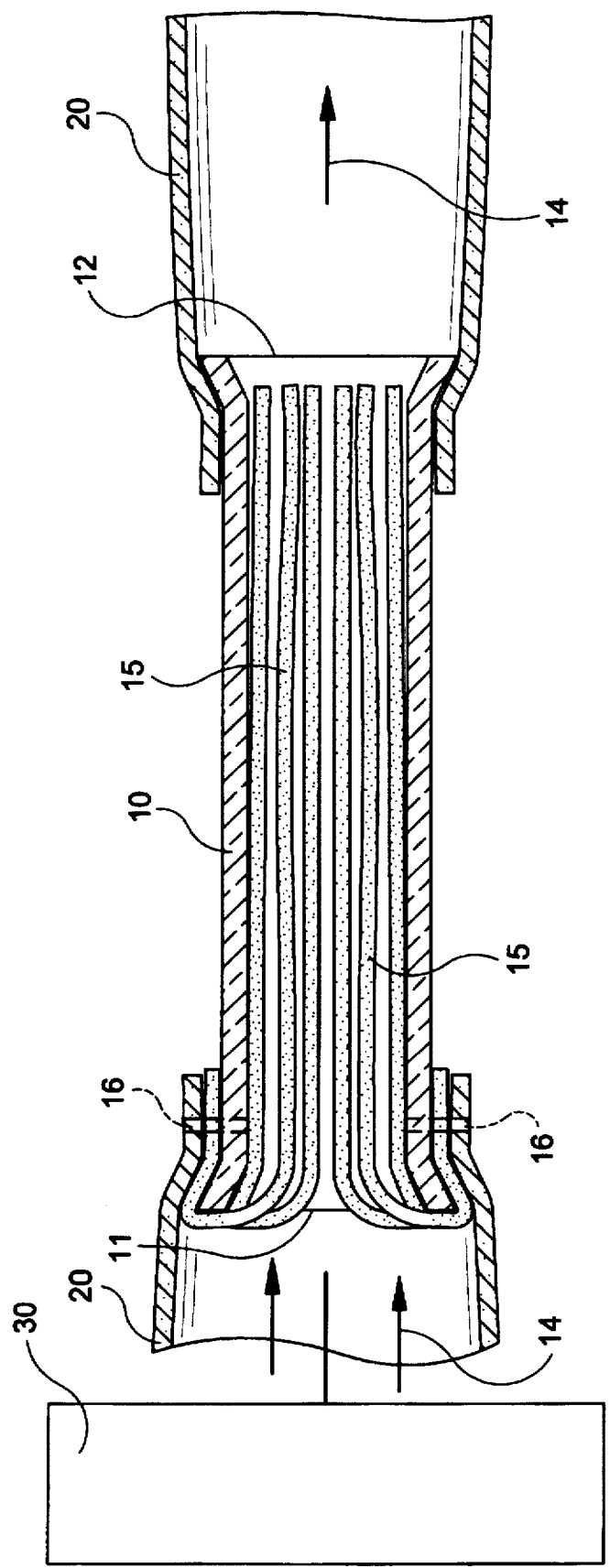

CARDIOVASCULAR TESTING DEVICE

FIELD OF THE INVENTION

The present invention relates to a cardiovascular testing device and in particular to a method and device for testing blood coagulation in animals.

BACKGROUND OF THE INVENTION

Deep vein thrombosis is a major health concern which affects many individuals. Many risk factors, such as immobilization, hypercoagulable states, tissue trauma, pregnancy or surgical recovery often contribute to this disease. To investigate potential antithrombotic agents to treat this and other thrombotic diseases, various experimental methods and devices have been developed and utilized. In order to simulate the pathologic processes in humans, thrombotic conditions have been created in animal models via various methods and devices, including creating vessel wall injury, tying-off of the vessels or introducing electric current through the vessel wall.

One common drawback to all known methods of studying thrombotic conditions is that the artificial creation of the thrombosis does not closely simulate the natural creation of a thrombosis within the human body. Consequently, no method or device exists which would allow for the testing of thrombotic situations under natural conditions. Many existing devices and methods require occlusion of blood vessels and thrombotic formation using blood that is not flowing. Such stasis is not a natural condition. Further, prior methods and devices do not allow for precise measurement of the blood flow through the thrombotic area or for the precise removal and measurement of the thrombus. Accordingly, it would be beneficial to provide a device which would allow for testing of thrombotic situations under more naturally occurring conditions.

SUMMARY OF THE INVENTION

The present invention relates to a method and device for creating and testing arterial and venous thrombotic conditions. The invention comprises a tube which is inserted into a blood vessel of an animal. The tube contains one or more strands upon which various materials, such as procoagulants or anticoagulants may be placed. Blood flows through the tube and clots form on the threads. After the completion of the test, the tube is removed from the animal, the strands are removed from the tube and the clots may be measured and weighed and otherwise analyzed. In a preferred embodiment, a flowmeter may be connected to the blood vessel to measure the blood flow so that the clot measurements may be correlated with the blood flow.

BRIEF DESCRIPTION OF THE DRAWINGS

FIG. 1 is a perspective view of a first embodiment of the device of the present invention in use.

FIG. 2 is a perspective view of a second embodiment of the device of the present invention in use.

DETAILED DESCRIPTION OF THE INVENTION

The cardiovascular testing device of the present invention is illustrated in FIGS. 1 and 2. Shunt 10 is in the form of a hollow tube having entrance opening 11 and exit opening 12. For use in testing, shunt 10 is inserted within an opening in a blood vessel 20. The shunt may be made of various materials, however preferably the shunt is made of plastic, with a preferred material being PE-280 tubing. Preferably, the shunt is clear so that clot formation within the shunt may be observed from outside of the shunt. The shunt may also be siliconized so that it is anti-thrombotic.

The shunt may be of any length and diameter so that it will fit within the blood vessel involved in the testing. A preferred length for the shunt is in the range of from about 1 cm. to about 5 cm. This length should allow for use in many common animal models such as rabbits. The diameter of the shunt is preferably within the range of from about 1 mm. to about 25 mm., with an especially preferred diameter in the range of from about 2 mm. to about 4 mm. This diameter provides easy testing in common laboratory animals such as rabbits. The two ends of the shunt may be flared outward to enable the shunt to be firmly affixed within the blood vessel.

Strands 15 are located within the shunt. The strands serve as a thrombogenic surface to initiate thrombus formation. The strands are affixed via a fastening means to the outside of the shunt near the entrance opening and extend throughout the length of the shunt such that they are hanging in the direction of the blood flow, as illustrated by arrows 14. In the preferred embodiment, the strands extend throughout the length of the shunt, but do not extend beyond the exit opening of the shunt. This preferred embodiment allows for more precise measurement of clot formation within the shunt. A preferred fastening means for affixing the strands to the outside of the shunt is a fastening loop 16 which wraps around the ends of the strands and pinches them tightly to the outer surface of the shunt. Such a wrapping is desirable because it allows for easy removal of the strands from the shunt following the completion of the test. The strands preferably consist of a multi-filament thread having a large surface area so as to provide the maximum area for clot formation. Cotton is the preferred material for the strands, with a preferred cotton being cotton umbilical tape marketed by Ethicon, Inc., Somerville, N.J.

The strands may be either coated or uncoated. Potentially useful coatings may consist of any material which modifies platelet adhesion, platelet aggregation and/or inhibits or enhances clotting. One method of treating the strands is to place them in rabbit plasma, incubate them and then add thrombin and calcium to create a fibrin coating which promotes clotting. In order to create an anti-coagulant effect, an additional material may be placed over the fibrin or else defective fibrin may be used. By coating the threads it is possible to test the effectiveness of various interventions which are designed to modify platelet plug or blood clot formation. Depending upon the parameters of the test, including the species being used, the size of the shunt and the rapidity of the thrombosis desired, various numbers of strands may be employed, with a range of from one strand to about 25 strands being preferred. For tests employing rabbits, preferably about six uncoated strands, as illustrated in FIG. 2, are used, while if the strands are coated the preferred number of strands is about three, as illustrated in FIG. 1.

The shunt is used by placing it in a blood vessel, either an artery or a vein, of an approximately similar diameter to that of the shunt. The shunt may be affixed to the blood vessel through a friction fit or it may be fastened by a fastening means, such as a fastening loop of string. Blood is allowed to flow through the shunt and come into contact with the threads. As the blood flows through the shunt, platelet plug and blood clot formation on the threads may be measured. In a preferred embodiment, a blood flowmeter 30 is attached to the blood vessel being tested and the blood flow through the shunt is measured. Examples of types of flowmeters which may be employed are Doppler, transonic or EMF, with a preferred flowmeter being the T206 dual channel flowmeter manufactured by Transonic Systems, Inc., Ithaca, N.Y. Such measuring allows an accurate estimation of the rate of blood clot formation and the time to occlusive thrombus formation. Further, the effectiveness of different interventions, pharmacologic or physiological, designed to modify platelet plug or blood clot formation may be measured with this method by determining and comparing the time to occlusive thrombus formation, the rate of thrombus formation as defined by changes in blood flow, the size of the thrombus and the composition of the thrombus.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

We claim:

1. A cardiovascular testing device, comprising a hollow tube having an entrance opening and an exit opening and one or more strands extending through the hollow tube wherein the one or more strands are comprised of multi-filament thread and are affixed to the hollow tube at a point adjacent to the entrance opening, and wherein the one or more strands comprises in the range of from one strand to about 25 strands and the strands are coated with material selected from the group consisting of coagulants, anticoagulants and mixtures thereof.

2. A cardiovascular testing device according to claim 1, wherein the multi-filament thread is cotton.

3. A cardiovascular testing device according to claim 1 having in the range of from about three to about six threads.

4. A cardiovascular testing device according to claim 1 wherein the one or more strands have a length in the range of from about 1 cm. to about 5 cm.

5. A cardiovascular testing device according to claim 1, wherein the hollow tube has a diameter in the range of from about 1 mm. to about 25 mm.

6. A cardiovascular testing device according to claim 1, wherein the hollow tube is coated with an anticoagulant.

7. A cardiovascular testing device according to claim 1, wherein the hollow tube is clear.

8. A method of testing blood coagulation comprising the step of inserting the cardiovascular testing device of claim 1 into a blood vessel.

9. The method according to claim 8, further including the step of inserting the cardiovascular device in a blood vessel such that blood flows through the hollow tube and blood clots form on the one or more strands.

10. The method according to claim 9, further including the step of utilizing a flow meter on the blood vessel at a point adjacent to the cardiovascular testing device.

11. A method of testing blood coagulation comprising the steps of:

inserting a hollow tube containing one or more strands within a blood vessel;

passing blood through the hollow tube such that the blood comes into contact with the one or more strands, allowing proper conditions for clots to form on the strands; and removing the hollow tube from the blood vessel; wherein the strands are comprised of multi-filament thread and the one or more strands comprises in the range of from one strand to about 25 strands and wherein the strands are coated with material selected from the group consisting of coagulants, anticoagulants and mixtures thereof.

12. A method of testing blood coagulation according to claim 11 further comprising the step of providing cotton multi-filament thread.

13. A method of testing blood according to claim 11 further comprising the step of providing in the range of from about three to about six strands.

14. A method of testing blood coagulation according to claim 11 further comprising the step of providing the one or more strands with a length in the range of from about 1 cm. to about 5 cm.

15. A method of testing blood coagulation according to claim 11 further comprising the step of providing the hollow tube with a diameter in the range of from about 1 mm. to about 25 mm.

16. A method of testing blood coagulation according to claim 11 further comprising the step of coating the hollow tube with an anticoagulant.

17. A method of testing blood coagulation according to claim 11 further comprising the step of providing a clear hollow tube.

* * * * *